United States Patent
Parker et al.

(10) Patent No.: US 7,272,446 B2
(45) Date of Patent: Sep. 18, 2007

(54) POWER EFFICIENT ELECTRICAL STIMULATION

(75) Inventors: John Parker, Roseville (AU); James F. Patrick, Roseville (AU)

(73) Assignee: Cochlear Limited, Lane Cove, NSW (AU)

( * ) Notice: Subject to any disclaimer, the term of this patent is extended or adjusted under 35 U.S.C. 154(b) by 570 days.

(21) Appl. No.: 10/343,397

(22) PCT Filed: Aug. 21, 2001

(86) PCT No.: PCT/AU01/01032

§ 371 (c)(1),
(2), (4) Date: Feb. 21, 2003

(87) PCT Pub. No.: WO02/17679

PCT Pub. Date: Feb. 28, 2002

(65) Prior Publication Data

US 2003/0163172 A1  Aug. 28, 2003

(30) Foreign Application Priority Data

Aug. 21, 2000 (AU) .................................. PQ9528

(51) Int. Cl.
*A61N 1/18* (2006.01)

(52) U.S. Cl. .............. 607/57; 607/2; 607/55; 607/56; 607/136; 607/137; 600/25; 623/10

(58) Field of Classification Search ............ 607/55–57, 607/2, 45, 43, 48, 136–137; 600/25; 623/10
See application file for complete search history.

(56) References Cited

U.S. PATENT DOCUMENTS

| | | | |
|---|---|---|---|
| 4,532,930 A | * | 8/1985 | Crosby et al. ................ 607/57 |
| 5,895,416 A | * | 4/1999 | Barreras et al. .............. 607/62 |
| 6,463,328 B1 | * | 10/2002 | John ........................... 607/45 |
| 6,537,200 B2 | | 3/2003 | Leysieffer et al. |
| 6,565,503 B2 | | 5/2003 | Leysieffer et al. |
| 6,575,894 B2 | | 6/2003 | Leysieffer et al. |
| 6,697,674 B2 | | 2/2004 | Leysieffer et al. |
| 6,751,505 B1 | * | 6/2004 | Van Den Honert et al. ... 607/57 |
| 2004/0098063 A1 | * | 5/2004 | Goetz .......................... 607/48 |

FOREIGN PATENT DOCUMENTS

| | | |
|---|---|---|
| EP | 0 282 336 A | 9/1988 |
| WO | WO93/24176 A1 | 12/1993 |
| WO | WO95/01709 A1 | 1/1995 |
| WO | WO96/12383 A1 | 4/1996 |
| WO | WO97/48447 A | 12/1997 |

OTHER PUBLICATIONS

International Search Report dated Oct. 5, 2001; counterpart patent application PCT/AU01/01032 filed Aug. 21, 2001; Publication No. WO 02/17679; Publication Date Feb. 28, 2002: Inventors: John Parker et al: Applicant: Cochlear Limited.

(Continued)

*Primary Examiner*—Carl Layno
*Assistant Examiner*—Shevon Johnson
(74) *Attorney, Agent, or Firm*—Connoly Bove Lodge & Hutz, LLP

(57) ABSTRACT

A method and device are disclosed for neural stimulation with improved power consumption and/or effectiveness. The stimulus generator is arranged, for example via a look up table, to recognize proposed stimuli which will be masked by earlier or simultaneous stimuli. Such masked stimuli are either deleted, or replaced by another stimulus.

12 Claims, 2 Drawing Sheets

OTHER PUBLICATIONS

International Preliminary Examination Report dated Apr. 10, 2002; counterpart patent application PCT/AU01/01032 filed Aug. 21, 2001; Publication No. WO 02/17679; Publication Date Feb. 28, 2002: Inventors: John Parker et al: Applicant: Cochlear Limited.

Supplementary European Search Report dated Aug. 11, 2005.

Bernd Edler, Heiko Purnhagen, and Charalampos Ferekidis, *ASAC - Analysis/Synthesis Audio Codec for Very Low Bit Rates*, 100th AES Convention, Copenhagen (May 1996).

Frank Baumgarte, Charalampos Ferekidis, and Hendrik Fuchs, *A Nonlinear Psychoacoustic Model Applied to the ISO MPEG Layer 3 Coder*, 99th AES Convention, New York (Oct. 1995).

Lawrence T. Cohen, Louise M. Richards, Elaine Saunders, and Robert S.C. Cowen, *Spatial Spread of Neural Excitation in Cochlear Implant Recipients: Comparison of Improved ECAP Method and Psychophysical Forward Masking*, 179 Hearing Res. 72-87 (May 2003).

Abbas PJ, Brown CJ, Hughes ML, Ganz BJ, Wolaver AA, Gervais JP and Hong SH, *Electrically evoked compound action potentials recorded from subjects who use the nucleus CI24M device*, 185 Ann Otol Rhinol Laryngol Suppl. 6-9 (Dec. 2000).

Lawrence T. Cohen, Elaine Saunders, and Louise M. Richardson, *Spatial Spread of Neural Excitation: Comparison of Compound Action Potential and Forward-Masking Data In Cochlear Implant Recipients*, 43 International Journal of Audiology 346-355 (2004).

Miller CA, Abbas PJ, Brown CJ, *An Improved Method of Reducing Stimulus Artifact in the Electrically Evoked Whole Nerve Potential*, 21(4) Ear Hear 280-90 (Aug. 2000).

\* cited by examiner

POWER EFFICIENT ELECTRICAL STIMULATION

TECHNICAL FIELD

The present invention relates to devices and methods for neural stimulation, and particularly but not exclusively to auditory prostheses.

BACKGROUND ART

Wearable medical devices reliant upon stored power share a common dynamic. As the possible and desired functionality of the devices is improved, the power demands generally also increase. As a result, the life per charge or per cell is reduced, which has not only a cost impact for the user, but also increases the risk that a device will power down at an inconvenient time.

In the field of cochlear implants, this issue is exacerbated by the trend to a single, behind the ear unit to replace what was once a head mounted unit and a separate speech processor unit worn on the body. The available volume and weight for the power cell is accordingly reduced. Increased power demands to provide improved functionality create a need to consider the efficiency of speech processing schemes and stimulus sets in order to provide maximum battery life.

It is an object of the present invention to provide an improved processing method and device, in order to a better balance of power consumption and performance in neural stimulation systems, particularly auditory prostheses.

SUMMARY OF THE INVENTION

The present invention provides, broadly, for a scheme in which masking effects are taken into account when determining which stimuli are actually delivered to a patient. This may be implemented in various ways. In one approach, after a set of stimulus instructions is generated, the set is checked against a look-up table. This table contains combinations of stimuli which have previously been clinically determined for that patient to display a masking effect. The second stimulus is deleted in this case.

In another approach, a theoretical model of masking could be used in addition to or instead of a look up table.

According to one aspect, the present invention relates to a method of neural stimulation of the type in which successive stimuli are presented on an electrode array having one or more electrodes, said stimuli being generated by a stimulus generation device, the method including the steps of:
  determining a stimulus set for one or more periods;
  analyzing each proposed stimulus set using a predetermined instruction set which is adopted to locate factors indicative of a likely masking effect;
  if masking effects are detected, altering said stimulus set for one or more of said periods;
  presenting the stimuli via said electrode array to a neural structure.

According to another aspect, the present invention provides a neural stimulator device, including a stimulus generation device for generating stimulus sets for one or more periods, said stimulus sets being intended for delivery at an electrode array for operatively presenting stimuli to neural structures,
  wherein said device further includes processing means implementing a predetermined instruction set, said processing means analyzing each stimulus set using said predetermined instruction set in order to locate factors indicative of a likely masking effect, and if it is determined that a masking effect is likely, altering said stimulus set.

The stimulus set may include a single stimulus in which case only the variable parameters relevant to that type of stimulation need to be specified. In suitable devices, this may include the timing, waveform, frequency, current, voltage, phase, amplitude and electrode location or further factors as required. The instruction set in this case preferably will consider the stimuli previously delivered in determining whether a masking effect is likely.

Alternatively, the stimulus set may include multiple stimuli, with variables as discussed above. If this case, in addition to or instead of previous stimulus sets, the instruction set will preferably analyses the various stimuli in relation to each other.

The stimulus generation device may be unitary or be made of physically distinct parts. For example, in the case of a cochlear implant, it may include both an external speech processor and an implanted device, only the speech processor, or only an implanted device, depending upon the desired location of processing capacity. The instruction set may be implanted as a separate procedure, or integrated within the processor which generates the stimulus set.

In a preferred form, if analysis indicates a likelihood of masking, the masked stimulus is simply omitted. However, in a system such as a cochlear implant, where stimuli are presented on multiple electrodes, an alternative stimuli—for example, on a different electrode—may be substituted. For example, the next most significant sound channel may be selected as the basis for stimulation.

In the case of the intra-cochlear implant, it has been observed that certain stimuli, when delivered simultaneously or in close succession, do not produce a patient percept significantly different from when only the first stimulus is delivered. For example, consider a conventional, multi-electrode intra-cochlear electrode array. If a large amplitude stimulus is delivered at one electrode, and simultaneously a smaller amplitude stimulus is delivered at the next electrode, then in many cases the user will not be able to perceive whether or not the smaller stimulus was delivered—it is said to be masked by the large stimulus. Other circumstances may give rise to masking of various neural percepts. Masking phenomena have been discussed in the technical literature.

The present invention arises from a recognition that masking effects can be considered as indicating a waste of stimulation power, as although the stimulus is presented to the patient, the patient does not receive any increased perception as a result of the stimulus. Accordingly, a proportion of the stimulus energy is simply wasted.

BRIEF DESCRIPTION OF DRAWINGS

An implementation of the present invention will now be described with reference to the accompanying figures, in which.

The present invention will be described with particular reference to a speech processor unit for a cochlear implant system. However, it will be appreciated that the present invention has application to other neural stimulation systems where the masking phenomenon may be relevant.

Figure 1:
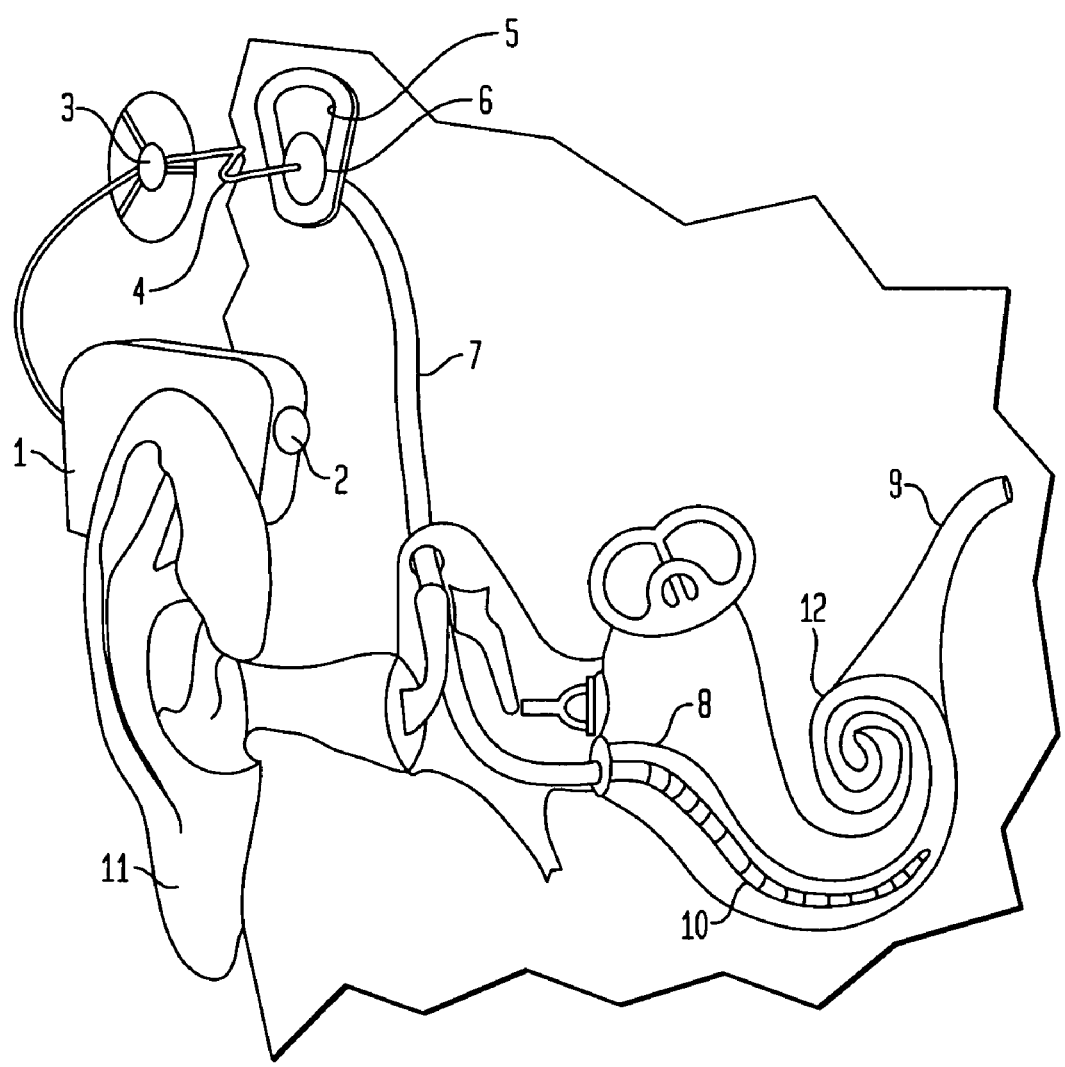
FIG. 1 is a schematic illustration of a conventional intra-cochlear implant system.

Referring to FIG. 1, a typical cochlear implant device is shown. The external component, includes a speech processor 1, and a microphone 2. The speech processor is in this illustration constructed and arranged so that it can fit behind the outer ear 11. Attached to speech processor 1 is a transmitter coil 3 which transmits the electrical signals to the implanted unit 5 via an RF link 4.

The implanted component 5 includes a receiver coil 6 for receiving power and data from coil 3. A cable 7 extends from the implanted device 5 to the cochlea 12 and terminates in an electrode array 10. The signals thus received are applied by the array 10 to the basilar membrane 8 thereby stimulating the auditory nerve 9.

Thus, the RF link, which is in turn powered by the speech processor 1, provides power and data to the implanted device 6. The speech processor also processes sound signals received by microphone 2, so as to send appropriate instructions for stimulation to the implanted device 6. The precise details of speech processing are not necessary for an understanding of the present invention, and are in any case well understood by those skilled in the art. Any suitable speech processing strategy could be used in conjunction with the present invention.

Figure 2:
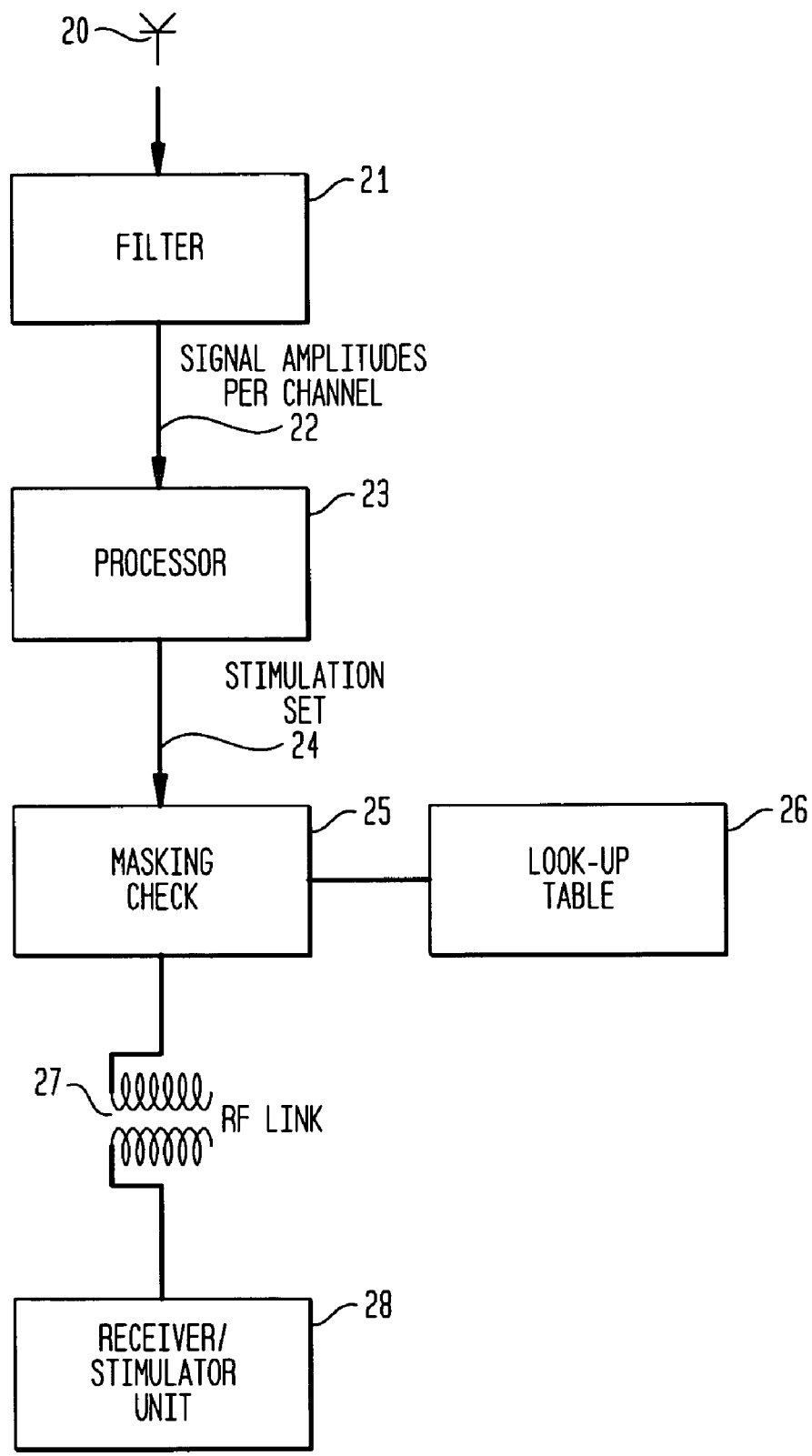
FIG. 2 is a block diagram illustrating the operation of one embodiment of the inventive system.

The block diagram of FIG. 2 illustrates one implementation of the present invention, in schematic terms.

Sound signals are detected by microphone 20, and processed into a predetermined number of frequency channels by filter 21. The output of filter 21 is a set of signal amplitudes per channel 22. Processor 23, in simple terms, selects certain channels as the basis for stimulation, based on amplitude or other factors. A set of stimulation instructions for implanted receiver stimulator unit 28 is thereby produced.

These instructions include at least the electrode or electrodes to be stimulated, and the amplitude of the stimulus to be applied. The process so far is conventional.

Masking check 25 involves comparing each successive two or more stimuli with the look-up table to determine whether they match a predetermined masking rule in look-up table 26.

The table below sets out a set of minimum unmasked level—that is, for one electrode n, the level which will not be masked, as a function of the stimulus levels which have been applied to the other electrodes within the previous $2m^5$. The electrode column lists the electrodes in an array of n max electrodes. Each entry M gives the minimum stimulus level (amplitude) to electrode n which will elicit a response immediately following a stimulus to the relevant electrodes, expressed as values between threshold (T) and maximum comfortable (c) levels. It will be appreciated that T and C levels are routinely determined during set up of a speech processor.

Minimum Unmasked Level

| Electrode | |
|---|---|
| 1 | $M_{1,T} M_{1,T+1}$-----------$M_{1,c-1} M_{1,C}$ |
| 2 | |
| ⁞ | |
| n − 1 | $M_{n-1,T} M_{n-1,T+1}$------------$M_{n-1,C}$ |
| n − 1 | |
| ⁞ | |
| N max | |

The masking check output is thus, the stimulation set 24 with masked stimuli excluded. This is then transmitted conventionally, for example via an RF link 27 to the implanted receiver/stimulator unit, which operates conventionally.

Variations and additions will be apparent to those skilled in the art with the broad scope of the present invention.

The invention claimed is:

1. A method for successively presenting neural stimuli on an electrode array having one or more electrodes, comprising:
    determining a stimulus set for one or more periods;
    analyzing each proposed stimulus set using a predetermined instruction set which is adapted to locate factors indicative of a likely masking effect;
    if masking effects are detected,
        deleting at least one of said stimuli in said stimulus set, and
        adding at least one alternative stimuli to said stimulus set; and
    presenting the stimuli via said electrode array to a neural structure.

2. A method according to claim 1, wherein the predetermined instruction set is responsive to stimuli in previous periods.

3. A method according to claim 1, wherein the predetermined instruction set is responsive to the selected electrodes defined by said stimulus set.

4. A method according to claim 1, wherein if said predetermined instruction set determines that a stimulus will be masked, said stimulus is deleted from the stimulation set.

5. A method according to claim 1, wherein said neural stimulation is cochlear stimulation, and said stimulus generator includes an implanted component.

6. A method according to claim 5, wherein the predetermined instruction set is responsive to a look up table of stimuli which are likely to be masked.

7. A neural stimulator device comprising:
    a stimulus generation device for generating stimulus sets, said stimulation sets for delivery at an electrode array for operatively presenting stimuli to neural structures, each said stimulus set relating to one or more stimulation periods; and
    processing means for analyzing each stimulus set using a predetermined instruction set in order to locate factors indicative of a likely masking effect, and if it is determined that a masking effect is likely, for altering said stimulus set by deleting at least one of said stimuli in said stimulus set, and adding at least one alternative stimuli to said stimulus set; and
    means for presenting the stimuli via said electrode array to a neural structure.

8. A device according to claim 7, wherein the predetermined instruction set is responsive to stimuli in previous periods.

9. A device according to claim 7, wherein the predetermined instruction set is responsive to the selected electrodes defined by said stimulus set.

10. A device according to claim 7, wherein if said predetermined instruction set determines that a stimulus will be masked, said stimulus is deleted from the stimulation set.

11. A device according to claim 7, wherein said neural stimulation is cochlear stimulation, and said stimulus generator includes an implanted component.

12. A device according to claim 7, wherein the predetermined instruction set is responsive to a look up table of stimuli which are likely to be masked.

* * * * *

UNITED STATES PATENT AND TRADEMARK OFFICE
CERTIFICATE OF CORRECTION

PATENT NO. : 7,272,446 B2 Page 1 of 1
APPLICATION NO. : 10/343397
DATED : September 18, 2007
INVENTOR(S) : John Parker et al.

It is certified that error appears in the above-identified patent and that said Letters Patent is hereby corrected as shown below:

At column 3, line 11 reads "lating the auditory nerve 9." it should read

-- lating the auditory nerve 9. The operation of the device shown in figure 1 is described, for example, in US patent No. 4532930. --

In Claim 1, column 4, line 9 reads "A method for successively presenting neural stimuli on" and it should read -- A method for successively presenting stimuli on --.

Signed and Sealed this

Third Day of June, 2008

JON W. DUDAS
*Director of the United States Patent and Trademark Office*